United States Patent
Tsai et al.

(10) Patent No.: US 9,345,729 B2
(45) Date of Patent: May 24, 2016

(54) METHOD FOR TREATING OR PREVENTING HEART DISEASES

(71) Applicant: New Bellus Enterprises Co., Ltd., Tainan (TW)

(72) Inventors: Cheng-Chih Tsai, Taichung (TW); Chih-Yang Huang, Taichung (TW); Hsueh-Fang Wang, Taichung (TW); Chun-Hua Chen, Taichung (TW); Chun-Chih Huang, Tainan (TW)

(73) Assignee: NEW BELLUS ENTERPRISES CO., LTD., Tainan (TW)

( * ) Notice: Subject to any disclaimer, the term of this patent is extended or adjusted under 35 U.S.C. 154(b) by 0 days.

(21) Appl. No.: 14/547,933

(22) Filed: Nov. 19, 2014

(65) Prior Publication Data
US 2015/0150918 A1 Jun. 4, 2015

(30) Foreign Application Priority Data

Dec. 2, 2013 (TW) .............................. 102144116 A

(51) Int. Cl.
| | | |
|---|---|---|
| *A61K 35/74* | (2015.01) | |
| *A61K 35/747* | (2015.01) | |
| *A61K 35/744* | (2015.01) | |
| *A61K 35/745* | (2015.01) | |
| *A61K 35/00* | (2006.01) | |

(52) U.S. Cl.
CPC ............. *A61K 35/747* (2013.01); *A61K 35/744* (2013.01); *A61K 35/745* (2013.01); *A61K 2035/115* (2013.01)

(58) Field of Classification Search
None
See application file for complete search history.

(56) References Cited

U.S. PATENT DOCUMENTS

| | | | | |
|---|---|---|---|---|
| 8,349,337 | B1 * | 1/2013 | Farmer et al. .............. | 424/247.1 |
| 2012/0052047 | A1 * | 3/2012 | Lu et al. ........................ | 424/93.3 |

FOREIGN PATENT DOCUMENTS

TW  I434695  * 4/2014

OTHER PUBLICATIONS

Chiu, Y. Genotoxicity Assessment of Multispecies Probiotics . . . The Scientific World Journal 2013:1-7. 2013.*

* cited by examiner

*Primary Examiner* — Ralph Gitomer
(74) *Attorney, Agent, or Firm* — Ming Chow; Sinorica, LLC

(57) ABSTRACT

This invention discloses a method for treating or preventing heart diseases by using a probiotic composition. The method for treating or preventing heart diseases comprises administering to a subject an effective amount of a probiotic composition to prevent the myocardial cells from myocardial hypertrophy, fibrosis and apoptosis, wherein the probiotic composition comprising *Lactobacillus rhamnosus* LCR177 (BCRC910473), *Pediococcus acidilactici* PA318 (BCRC910474) and *Bifidobacterium adolescentis* (BCRC14609).

1 Claim, 19 Drawing Sheets

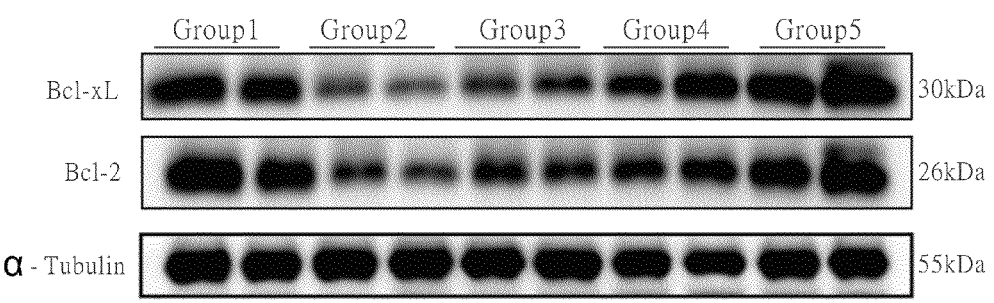
Fig. 14A
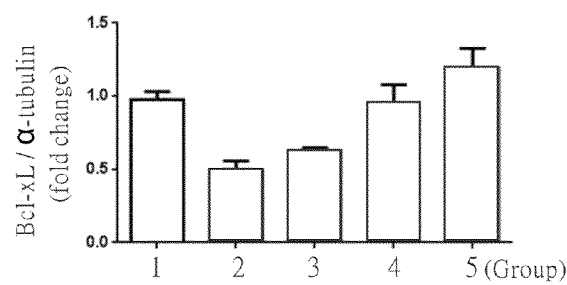 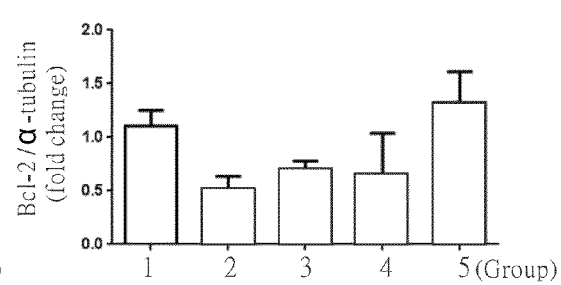
Fig. 14B　　　　　　　　　　Fig. 14C

METHOD FOR TREATING OR PREVENTING HEART DISEASES

The current application claims a foreign priority to the patent application of Taiwan No. 102144116 filed on Dec. 2, 2013.

BACKGROUND OF THE INVENTION

1. Field of the Invention

This present invention relates to a method for treating or preventing heart diseases, especially relates to a method for treating or preventing heart diseases by using a probiotic composition.

2. Description of the Related Art

Cardiovascular disease (CVD) has become a health issue to people all over the world. Statistically, about one-third population all over the world will die because of CVD. And in Taiwan, dead people from CVD are about one-fourth in all causes of death. Furthermore, CVD includes coronary heart disease (CHD), cerebrovascular disease and hypertensive heart disease, wherein CHD is the most popular heart disease and the major cause of sudden death. The main cause of CHD is atherosclerosis which is resulted from changing of the structure and composition of vascular intima to cause intravascular impaired blood flow or inadequate of blood flow. Therefore, when the atherosclerosis happens on coronary artery of heart, heart diseases symptoms such as myocardial infraction or angina pectoris will be triggered and necrosis and apoptosis of myocardial cells will be induced. Other research results show that the heart of adult mammals lack or have very poor ability of regeneration and the number of myocardial cells will never increase after born. But under outer stimulation, such as diseases, the myocardial cells will become bigger to expand and thicken heart muscles. This is so called the heart hypertrophy. The heart hypertrophy will gradually lead to deficiency of heart function and induce apoptosis of heart muscles. Whatever, individuals will become to a high risk group of the heart failure after apoptosis of myocardial cells, even dead in critical cases. Therefore, apoptosis of myocardial cells greatly affect health and life of a person.

Lactic acid bacteria which can ferment carbohydrate to lactic acid is widely found in nature, such as animals (raw milk or intestine) or plants (vegetables or fruits). Generally speaking, lactic acid bacteria include *Lactobacillus, Lactococcus, Leuconostoc, Pediococcus, Streptococcus, Aerococcus, Carnobacterium, Enterococcus, Oenococcus, Vagococcus, Weisella* etc., wherein the *Lactobacillus* have the most various species. Functionally speaking, lactic acid bacteria can be divided into non-intestine-lived and intestine-lived. Because the prior discoveries show that lactic acid bacteria can extend food storage time, improve food flavor and increase nutritional value, lactic acid bacteria is largely used in food processing industry. Recently, many researches discover that lactic acid bacteria can improve human health, such as lowering cholesterol in serum, increasing activities of immune system, modulating functions of gastrointestinal tract, inhibiting growth of pathogens and tumors. Base on its better safety of human body, lactic acid bacteria has become the most popular ingredient of food additives or dietary supplements.

SUMMARY OF THE INVENTION

This present invention relates to a method for treating or preventing heart diseases by using a probiotic composition. More specificity, the probiotic composition comprises *Lactobacillus rhamnosus* LCR177 (BCRC910473), *Pediococcus acidilactici* PA318 (BCRC910474) and *Bifidobacterium adolescentis* (BCRC14609) for protecting physical function of myocardial cells and decreasing apoptosis of myocardial cells.

One aspect of the invention is a method for treating or preventing heart diseases, comprising administering to a subject an effective amount of the probiotic composition to prevent or treat heart diseases, wherein the probiotic composition comprising *Lactobacillus rhamnosus* LCR177 (BCRC910473), *Pediococcus acidilactici* PA318 (BCRC910474) and *Bifidobacterium adolescentis* (BCRC14609).

Preferably, the heart diseases have symptoms such as myocardial hypertrophy, myocardial fibrosis or myocardial apoptosis.

Preferably, the probiotic composition includes *Lactobacillus rhamnosus* LCR177 (BCRC910473), *Pediococcus acidilactici* PA318 (BCRC910474) and *Bifidobacterium adolescentis* (BCRC14609) in a ratio of 1:1:1.

Another aspect of the invention is a probiotic composition which has the ability to protect the myocardial cells from apoptosis, so it can be used for treating or preventing heart diseases, wherein the probiotic composition comprising *Lactobacillus rhamnosus* LCR177 (BCRC910473), *Pediococcus acidilactici* PA318 (BCRC910474) and *Bifidobacterium adolescentis* (BCRC14609).

BRIEF DESCRIPTION OF THE DRAWINGS

FIG. 14A is the expressions of Bcl-2 and Bcl-xL in rat heart tissues from the groups 1 to 5.

FIG. 14B is the expression level of Bcl-xL in rat heart tissues from the groups 1 to 5.

FIG. 14C is the expression level of Phospho-Bcl-2 in rat heart tissues from the groups 1 to 5.

DETAILED DESCRIPTION OF THE INVENTION

Figure 1A:
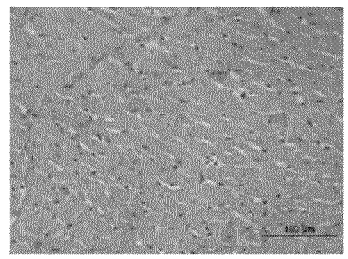
FIG. 1 A to FIG. 1 E show H&E stained sections of rat heart of the groups 1 to 5, respectively.
Figure 1B:
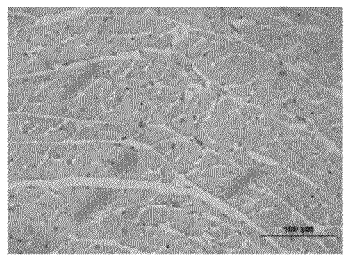
Figure 1C:
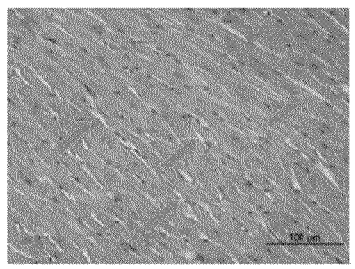
Figure 1D:
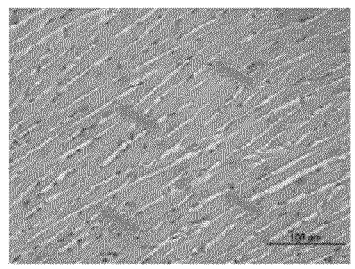
Figure 1E:
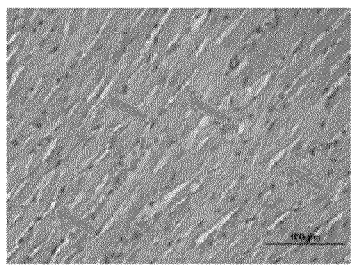
Figure 2A:
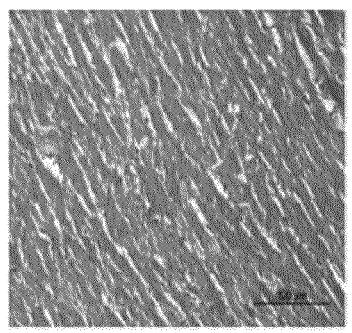
FIG. 2 A to FIG. 2 E show Masson's trichrome stained sections of rat heart of the groups 1 to 5, respectively. Masson's trichrome staining indicates collagen in blue.
Figure 2B:
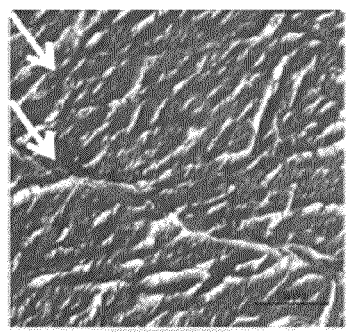
Figure 2C:
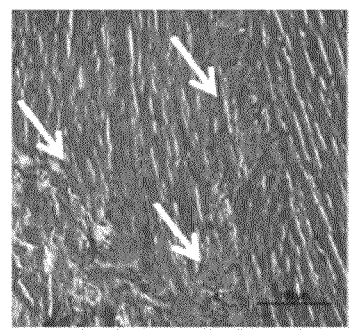
Figure 2D:
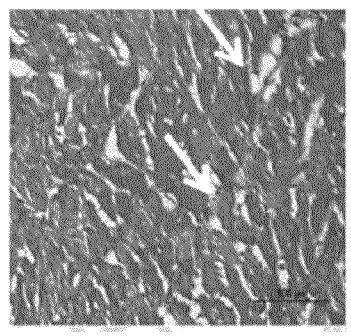
Figure 2E:
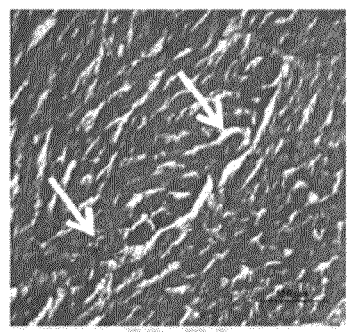
Figure 3A:
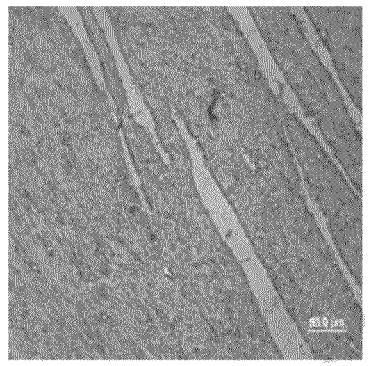
FIG. 3 A to FIG. 3 E show immunohistochemical stained sections of rat heart of the groups 1 to 5, respectively.
Figure 3B:
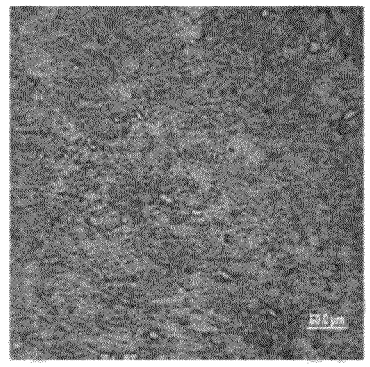
Figure 3C:
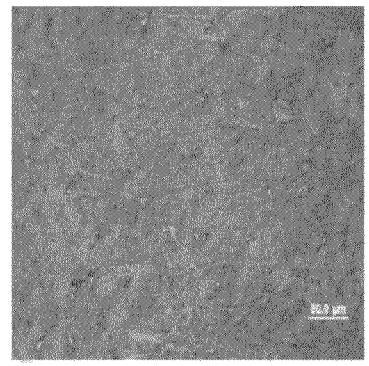
Figure 3D:
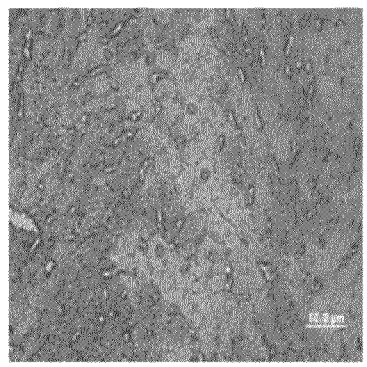
Figure 3E:
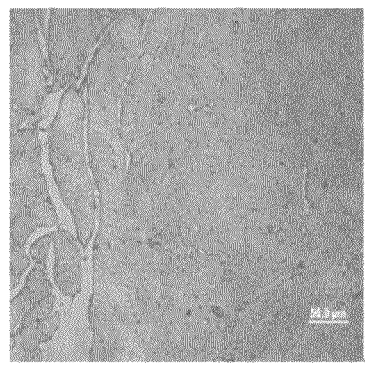

Hereinafter, there is an illustrative statement for the words mentioned by the specification and claims in this present invention, not to limit the specification and claims in this present invention.

Prior papers have disclosed about the apoptosis pathway which the protein hydroxylases will be triggered to execute apoptosis program when pro-apoptotic molecules activated. The effector caspases, such as caspase-3 and caspase-9, will be activated to split other proteins for initiating apoptosis process. The initiator caspases, such as caspase-8, work on upstream of the effector caspases to transfer signals of apoptosis from the cell membrane and the activate effector caspase.

According to the different activation pathway, the caspases are affected by different upstream pro-apoptotic factors. For example, the dephosphorylated Bad forms a dimer with the Bcl-2 family to induce mitochondria to release cytochrome C into the cytoplasm, and then activates the caspase 3 to cause apoptosis. If the Bad is phosphorylated by the Akt, PKA, Raf1, Rsk1, Pak1 etc., the Bad don't have any activity to form a dimer with the Bcl-2 family to induce apoptosis program. The other example is that when the Fas receptor binds with the Fas ligand, a part of the Fas receptor in the cytoplasm forms a death-inducing signaling complex (DISC) with the Fas-associating protein with death domain (FADD) and inactivated caspase-8. The activated caspase-8 which is produced by protein hydroxylase cuts the N-terminal region of the Bid to form truncated Bid (tBid). The tBid translocates to the mitochondria to induce release the cytochrome C release and apoptosis.

About the fibrosis of cells, the main mechanism is to increase expression level of connective tissue growth factor (CTGF) by activation downstream proteins of Erk1/2 kinase and SMAD family member 3 (Smad3). CTGF will proliferate fibroblasts around tissues and secret collagens to enhance and repair gaps between damage tissues for strengthening tissue structure. But if heart tissues rely on the mechanism to strengthen myocardial cells for long time, the myocardial cells will over-fibrosis to lose the original strength of contraction and relaxation and then cause disorder of blood output.

The term "autophagy" means a phenomenon of cell self-degradation and maintaining energy. Studies show that autophagy of cells is very important during the process of immune diseases, infectious diseases, inflammatory diseases, cancers, cardiovascular diseases etc. The autophagy-related gene (ATG) was found in the yeast. The Beclin 1, discovered by an American scientist, is the earliest found ATG from mammal.

The term "myocardial hypertrophy" means that muscles of heart are thickened or total volume of heart is expanded. It includes physiological and pathological hypertrophy. The pathological hypertrophy usually happens with different diseases, such as hypertension, aging or diabetes, and further can be categorized into concentric and eccentric hypertrophy. According prior studies, the concentric hypertrophy-related pathway is interleukin-6 (IL-6)/MEK/MAPK (mitogen-activated protein kinases)/GATA4 pathway and the eccentric hypertrophy-related pathway is IL-6/MEK5/ERK (extracellular regulated kinase)-5 or IL-6/JAK/STAT (signal transducers and activators of transcription)-3 pathway.

Hereinafter, there are several examples and figures to further illustrate this present invention.

The male Wistar rats in the following examples were bought from BioLASCO Taiwan Co., Ltd. at the age of 8 weeks.

EXAMPLE 1

Preparing Animal Model of Myocardial Damage

Plural male Wistar rats at the age of 8 weeks were feed in the following conditions: at regular diet, relative humidity of 60%, 25±1° C. of temperature, 12/12 light cycle. After feeding two weeks, the rats were randomly divided into 5 groups for 10 rats in the each group and then feed with different treatment, respectively. The group 1 was control group for delivering regular diet and normal water. The group 2 was feed high caloric feed. The group 3 was feed high caloric feed and low dose of the probiotic composition disclosed in this present invention. The group 4 was feed high caloric feed and middle dose of the probiotic composition disclosed in this present invention. The group 5 was feed high caloric feed and high dose of the probiotic composition disclosed in this present invention.

The probiotic composition includes *Lactobacillus rhamnosus* LCR177 (BCRC910473), *Pediococcus acidilactici* PA318 (BCRC910474) and *Bifidobacterium adolescentis* (BCRC14609) in a ratio of 1:1:1. The dose of the probiotic composition is according to a 60 kg weight adult to divide the human recommended dietary allowance of tested object to have the recommended dietary allowance of each kilogram weight. The recommended dietary allowance of each kilogram weight multiplied by the metabolic rate constant of experiment animal relative to human is the daily dose of experiment animal. Wherein, the metabolic rate constant of rat relative to human is 6.25. Therefore, the high dose for each rat is 0.1683 grams every day. The middle dose for each rat is 0.0168 grams every day. The low dose for each rat is 0.0017 grams every day.

The rats were sacrificed after feeding 8 weeks. Then, each rat's heart sample was harvested and withdrew the blood by cold phosphate buffered saline (PBS) and washed it. Residue fat and vascular tissues of each heart sample were removed and excess water was dried for the following examples.

EXAMPLE 2

Preparing Heart Sections

The heart tissues of the each group were fixed by 10% formalin at least 24 hours. The fixed heart tissues of left ventricle was proceeded the dehydration process by the following steps: soaked into PBS for about 30 minutes; soaked into 0.85% sodium chloride solution for about 30 minutes; and then put into 70%, 85%, 95% and 100% alcohol for 15, 30, 30 and 30 minutes, wherein soaking into 70% and 100% alcohol were repeated twice.

The dehydrated heart tissues were soaked into 100% xylene about 30 minutes, and repeat it once. Then, the heart tissues were soaked into 1:1 ratio of xylene and paraffin solution for 45 minutes under 60° C. After that, the heart tissues were soaked into 100% paraffin for about 20 minutes under 60° C. with 3 times repeated to finish paraffin-embedded of the heart tissues. The embedded heart tissues of the each group were cut into 0.2 μm of thickness sections, respectively, and then removed paraffin. After removing paraffin, the heart tissue sections of the each group were used for the following examples.

EXAMPLE 3

Staining Result of the Heart Tissue Sections of the Each Group

The heart tissue sections of the each group were stained by H&E and Masson's trichrome method. A Zeiss Axiophot dissecting microscope was used to observe the aliment of myocardial cells in the each group. The results were shown in FIGS. 1 and 2, wherein "A" to "E" in the figures were represent the results of heart tissue sections of the groups 1 to 5, respectively.

FIG. 1 shows that the gap between the myocardial cells in the group 2 was obviously larger than that in the group 1. Compared with the group 1, the gap between the myocardial cells in the groups 3 to 5 were smaller, respectively. Depending on the increasing dose of the probiotic composition in this present invention, the gap between the myocardial cells became smaller.

In FIG. 2, the arrows indicated the collagen accumulation among the cells. FIG. 2 shows that the gap between the myocardial cells in the group 2 not only increased but also accumulated large amount of collagen to trigger the fibrosis. However, the collagen accumulation in heart tissues of the groups 3 to 5 were significantly lower than that of the group 2, respectively.

The results showed that the heart tissues of the group 2 had pulled and dragged deformation and serious fibrosis, so that it could be sure to be recognized as the animal model of myocardial damages. Furthermore, the probiotic composition in this present invention had effects of decreasing the gap between the myocardial cells and easing fibrosis of heart tissues, and the effects were getting better with increasing feeding doses.

EXAMPLE 4

Immunohistochemical Staining for the Heart Tissue Sections of the Groups

Each of the heart tissue sections from example 2 was added LC3B primary antibody diluted for 100 times, and then overnight at 4° C. refrigerator. The DAB color development solution was added at room temperature for 2 hours. After phosphate buffered saline washed, the pictures of the heart tissue sections were taken by under microscopy. The results were shown in FIG. 3.

FIG. 3 shows that the expression level of LC3B from rats of the group 2 was significantly increased in comparison with the group 1. The expression of LC3B was inhibited in each of the groups 3 to 5, and the effect of inhibition was better when feeding dose increased.

EXAMPLE 5

Preparing the Protein Extractions of Heart Tissues of the Each Group

After isolation of the heart tissues from the each group, 100 mg of the isolated heart tissues from the each group was taken to add 1 mL protein extraction buffer ground by homogenizer at 4° C. and then separated into the eppendorf. Each of the homogenized protein solution was frozen and then centrifuged by 12000 g at 4° C. for 40 minutes to collect the supernatant. The collected supernatant was the protein extraction of heart tissue. All of the supernatants were preserved in the refrigerator under −80° C. for further uses.

EXAMPLE 6

Western Blotting

The protein extraction of the each group in example 5 was proceeded protein quantitation by Lowry method. The concentration of the each extraction was adjusted to 40 μg/μL. The protein extraction of the each group was separated by using 12% SDS-PAGE for gel electrophoresis with 75V for 150 minutes. Then, the proteins were transferred to the hybond-C PVDF membranes with 50V for 3 hours. The membranes were soaked into 3% BSA solution and added the primary antibody specific to the target protein. By staining with the antibody, it can observe the protein expression of the heart tissues of the each group.

EXAMPLE 7

Expressions of Myocardial Fibrosis Related Proteins in the Rat Heart Tissues from the Each Group Expression of myocardial fibrosis related proteins in the heart tissues from the each group were determined by the method described in example 6 including protein MMP2, MMP9 and TGF-β. The results were shown in FIG. 4 and the further Student's t test results were shown in FIG. 5.

Figure 4:
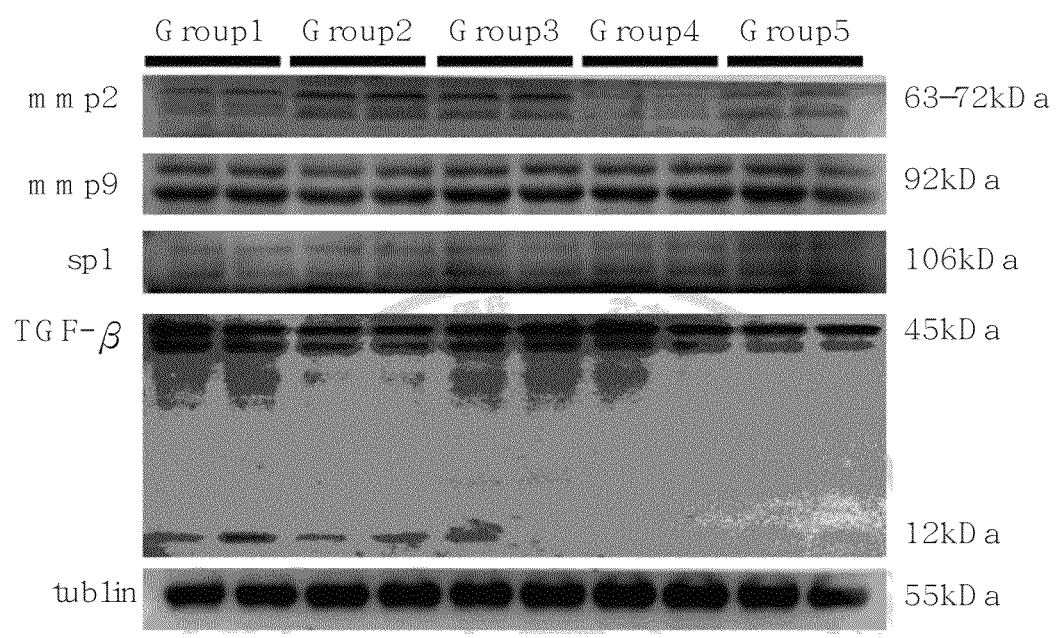
FIG. 4 is the expressions of myocardial fibrosis related proteins in rat heart tissues from the groups 1 to 5.
Figure 5A:
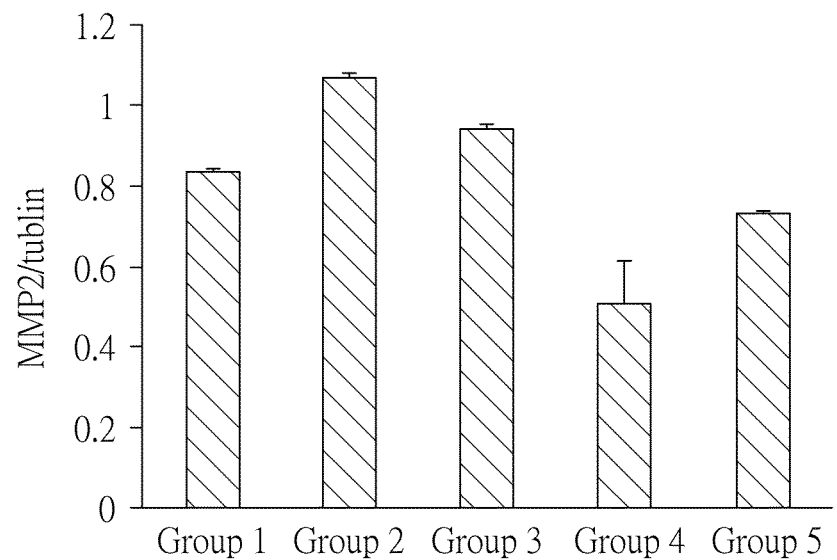
FIG. 5A is the expression level of MMP2 in rat heart tissues from the groups 1 to 5.
Figure 5B:
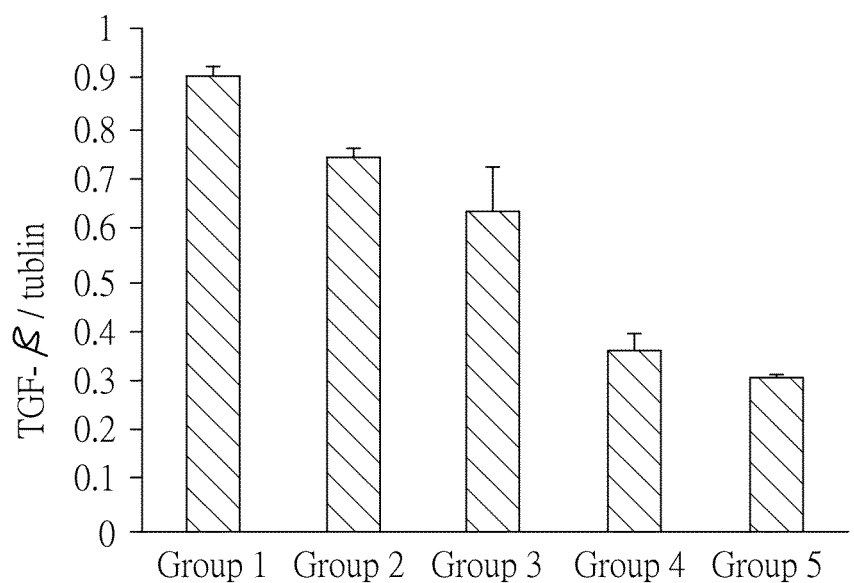
FIG. 5B is the expression level of TGF-$\beta$ in rat heart tissues from the groups 1 to 5.

The FIGS. 4 and 5 shows that the expression levels of MMP2 and activated TGF-β of the group 2 were all significantly increasing in comparison with that of the group 1. The expressions of the activated TGF-β and MMP2 of the group 3 were all decreasing in comparison with that of the group 2. The expression level of MMP2 of the groups 4 and 5 were significantly decreasing, respectively. Moreover, the expressions of activated TGF-β of the groups 4 and 5 were significantly inhibited, respectively.

The results illustrate that high calorie diet will significantly increase the expression levels of the markers of myocardial fibrosis, and it indicates that the heart has been suffered the damage from fibrosis and may cause symptoms such as inflexibility of heart muscles, cardiac atonia or heart failure. However, by the probiotic composition of this present invention, it can be obviously lowered the expression levels of the marker associated with myocardial fibrosis.

EXAMPLE 8

Expressions of Myocardial Autophagy Related Proteins in the Rat Heart Tissues of the Each Group Expressions of the myocardial autophagy related proteins in the rat heart tissues of the each group were determined by the method described in example 6 including protein Beclin-1, LC3B and ATG5. The results were shown in FIG. 6 and the further Student's t test results were shown in FIG. 7.

Figure 6:
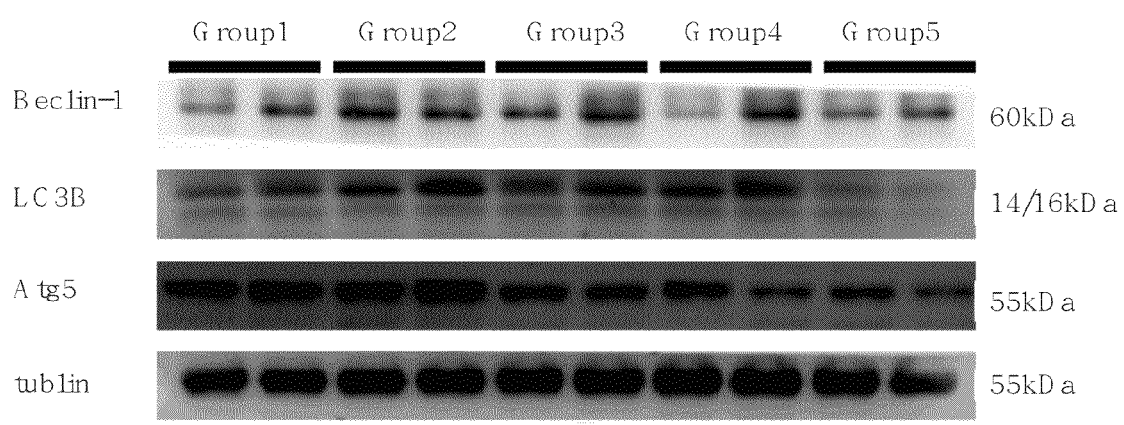
FIG. 6 is the expressions of myocardial autophagy related proteins in rat heart tissues from the groups 1 to 5.
Figure 7A:
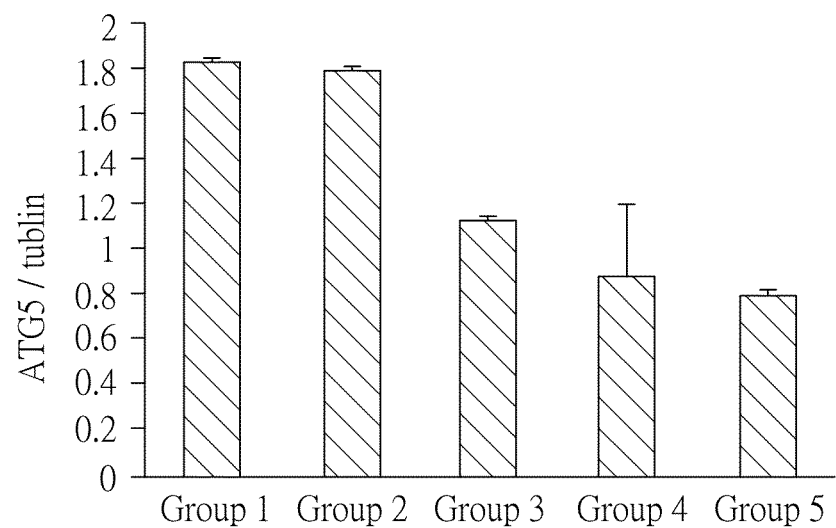
FIG. 7A is the expression level of ATG5 in rat heart tissues from the groups 1 to 5.
Figure 7B:
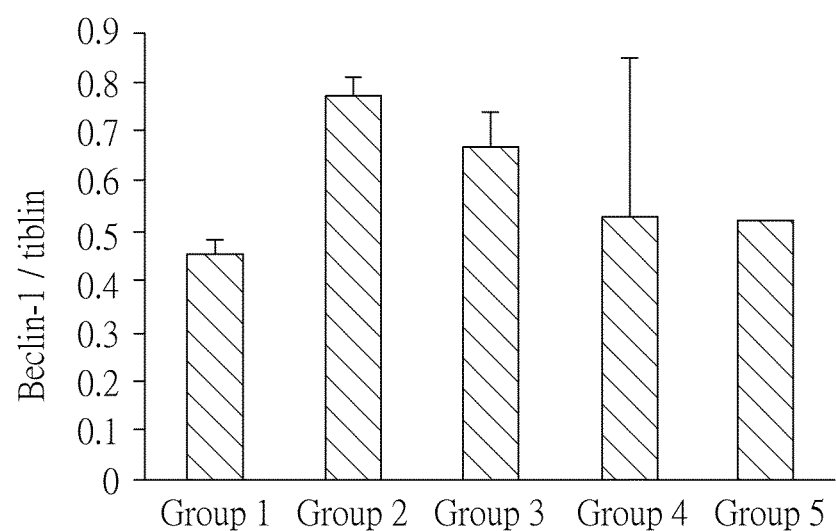
FIG. 7B is the expression level of Beclin-1 in rat heart tissues from the groups 1 to 5.
Figure 7C:
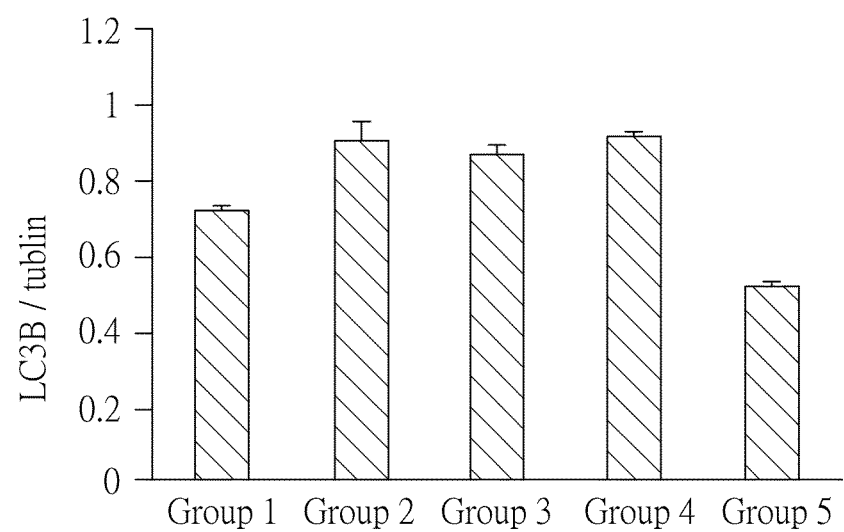
FIG. 7C is the expression level of LC3B in rat heart tissues from the groups 1 to 5.

FIGS. 6 and 7 show that the expression levels of Beclin-1, LC3B and ATG5 (autophagy-related gene 5) in the group 2 were all increasing in comparison with that in the group 1. Comparing with the group 2, the expression levels of Beclin-1, LC3B and ATG5 of the groups 3 to 5 were all significantly decreasing, respectively, and were declined larger according to the increasing feeding dose of the probiotic composition in this present invention.

Knowing from prior studies, the autophagy is the pathway for cleaning abnormal organelles or proteins to maintain the stable status of cell, renew the organelles of cell and providing energy. A cell will be damaged because of over-activation or decomposition when the balance of autophagy is interrupted. Therefore, according to the results of FIGS. 6 and 7, it shows that high calorie diet will increase the expression levels of the myocardial autophagy related proteins from the myocardial cells to cause heart damages in individuals. The expressions of the myocardial autophagy related proteins can be lowered by delivering the probiotic composition in this present invention. Moreover, according to the increasing dose of the probiotic composition, the expressions of the myocardial autophagy related protein in an individual with heart damages can be similar to that in a normal individual. Therefore, the probiotic composition in this present invention can indeed effectively prevent or treat heart damages or related diseases thereof.

EXAMPLE 9

Expressions of Myocardial Hypertrophy Related Proteins of the Each Group

Expressions of proteins such as ERK5, MEK5, uPA and ANP in the rat heart tissues of the each group were determined by the method described in example 6. The results were shown in FIG. 8, wherein the ERK5 and MEK5 are the marker proteins of eccentric hypertrophy pathway and the uPA and ANP are the marker proteins of pathological hypertrophy pathway. The further Student's t test results of the expression levels of the myocardial hypertrophy related proteins in the rat heart tissues of the each group were shown in FIG. 9.

Figure 8:
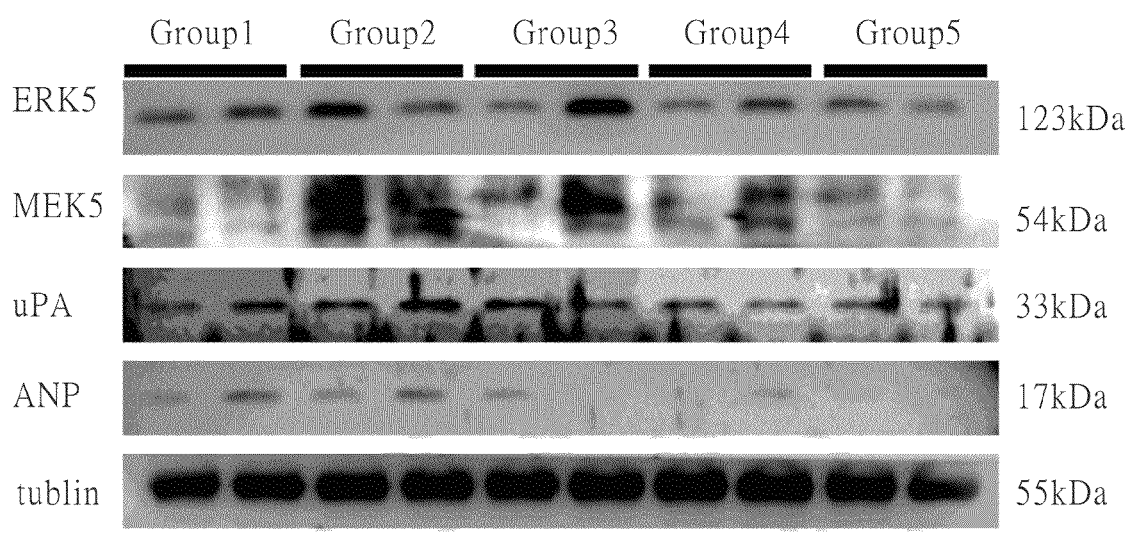
FIG. 8 is the expressions of myocardial hypertrophy related proteins in rat heart tissues from the groups 1 to 5.
Figure 9A:
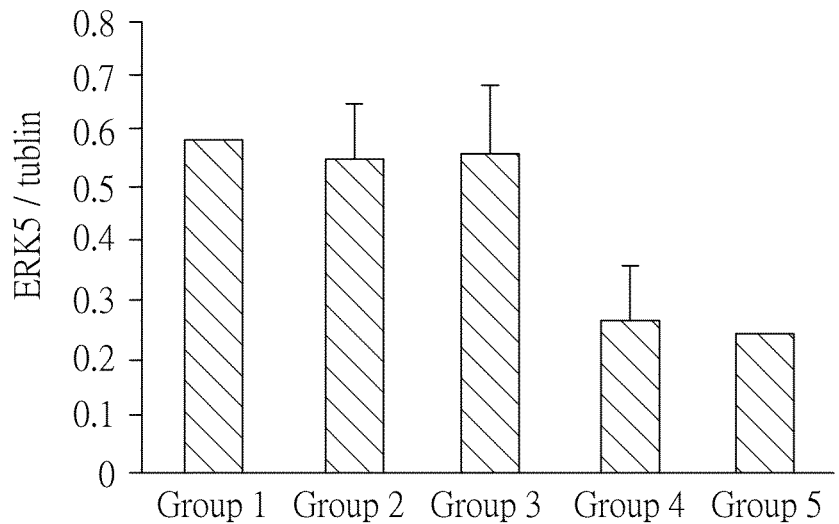
FIG. 9A is the expression level of ERK5 in rat heart tissues from the groups 1 to 5.
Figure 9B:
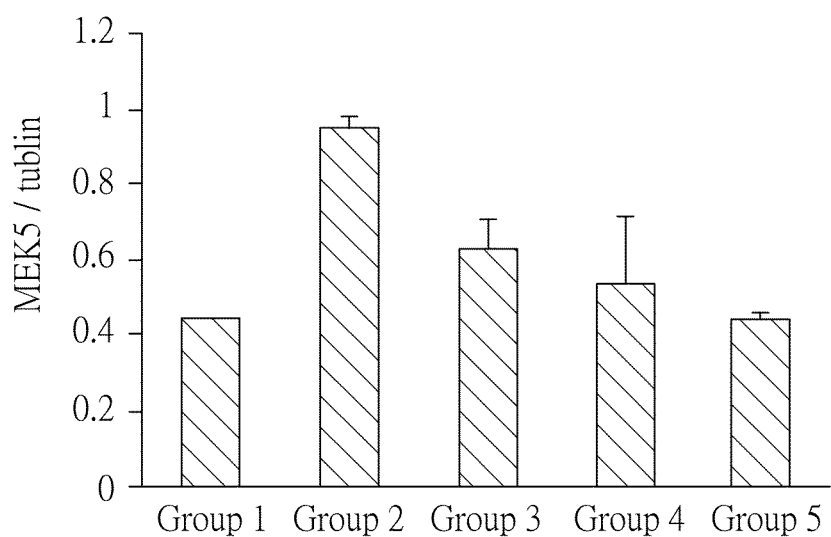
FIG. 9B is the expression level of MEK5 in rat heart tissues from the groups 1 to 5.
Figure 9C:
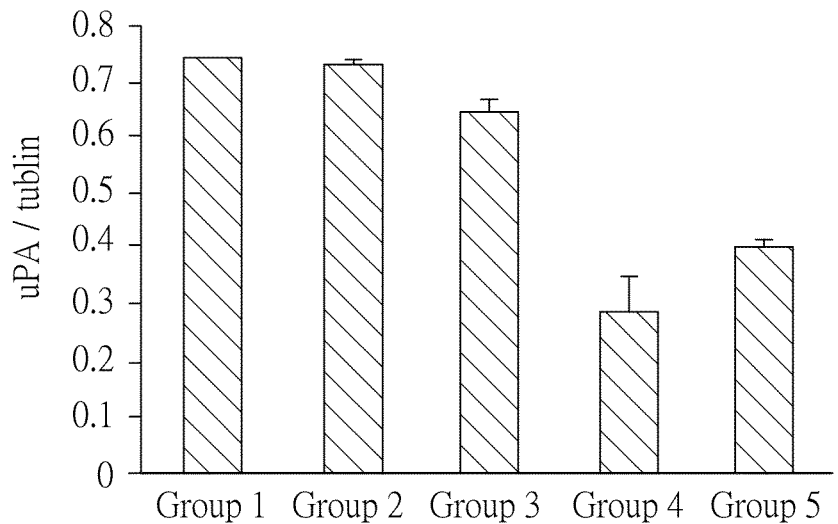
FIG. 9C is the expression level of uPA in rat heart tissues from the groups 1 to 5.
Figure 9D:
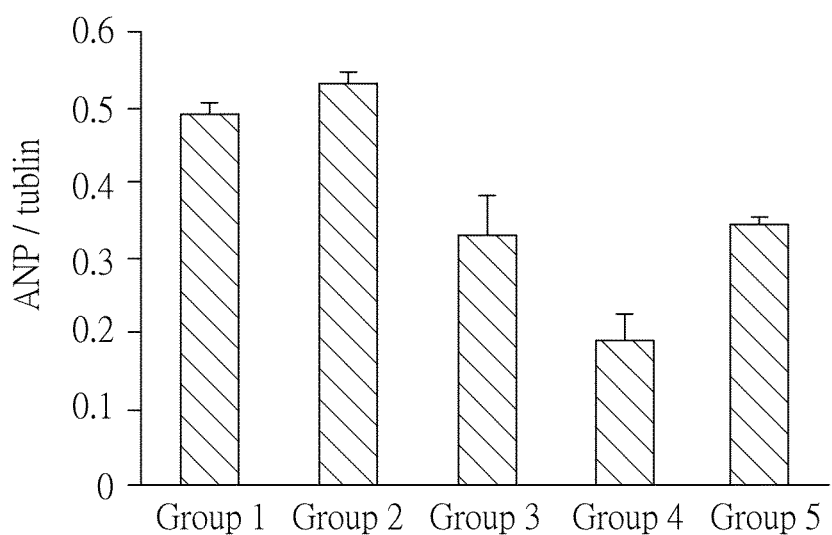
FIG. 9D is the expression level of ANP in rat heart tissues from the groups 1 to 5.

FIGS. 8 and 9 show that the expression levels of ERK5 and MEK5, the marker proteins of eccentric hypertrophy pathway, and uPA and ANP, the marker proteins of pathological hypertrophy pathway, of group 2 were all significantly increasing than that of group 1. However, the expression levels of ERK5, MEK5, uPA and ANP from the rat of the group 3 to 5 were significantly decreasing in comparison with that of the group 2, respectively, wherein the decreasing effect in the group 5 was the best. According to the results, it shows that high calorie diet will cause myocardial hypertrophy of an individual and heart damages. Delivering the probiotic composition disclosed in this present invention can prevent the damages of the individual heart from high calorie diet and effectively improve or treat heart hypertrophy thereof.

EXAMPLE 10

Expressions of Myocardial Apoptosis Related Proteins of the Each Group

Expressions of proteins such as FADD, truncated BID, caspase-8, Bad, phospho-Bad (p-Bad), Bcl-2, Bcl-xL, caspase 3, p-IGF1 receptor, phospho-PI3K (p-PI3K), phospho-Akt (p-Akt) in the rat heart tissues of the each group were determined by the method described in example 6. The results were shown in FIGS. 10 to 17.

Figure 10A:
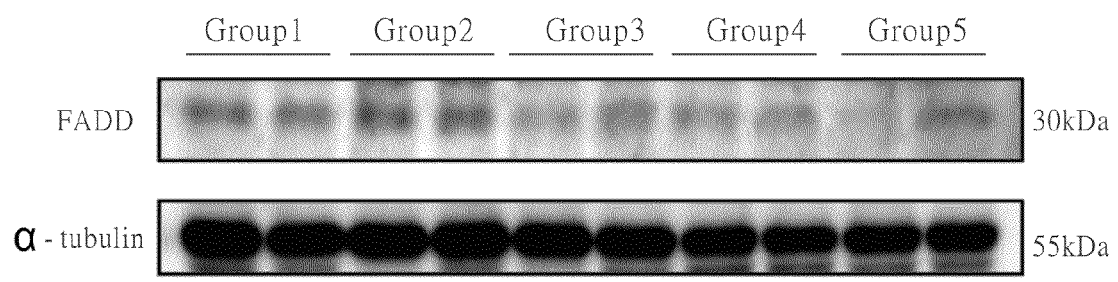
FIG. 10A is the expression of FADD in rat heart tissues from the groups 1 to 5.
Figure 10B:
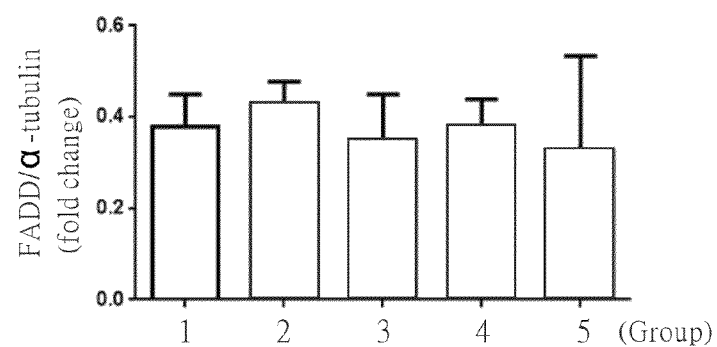
FIG. 10B is the expression level of FADD in rat heart tissues from the groups 1 to 5.

FIG. 10 illustrates that the expression level of FADD of the group 2 was increasing in comparison with that of the group 1. Comparing with the group 2, the expression levels of FADD of the groups 3 to 5 were all decreasing.

Figure 11A:
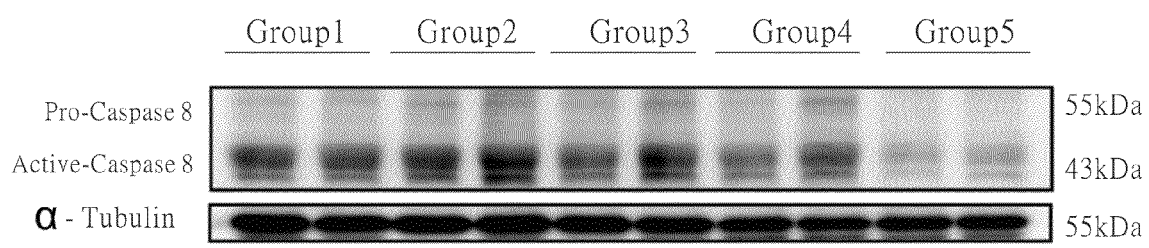
FIG. 11A is the expression of caspase 8 in rat heart tissues from the groups 1 to 5.
Figure 11B:
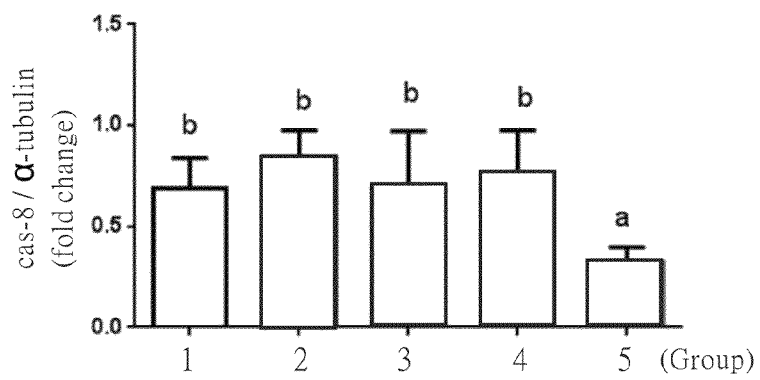
FIG. 11B is the expression level of caspase 8 in rat heart tissues from the groups 1 to 5.
Figure 12A:
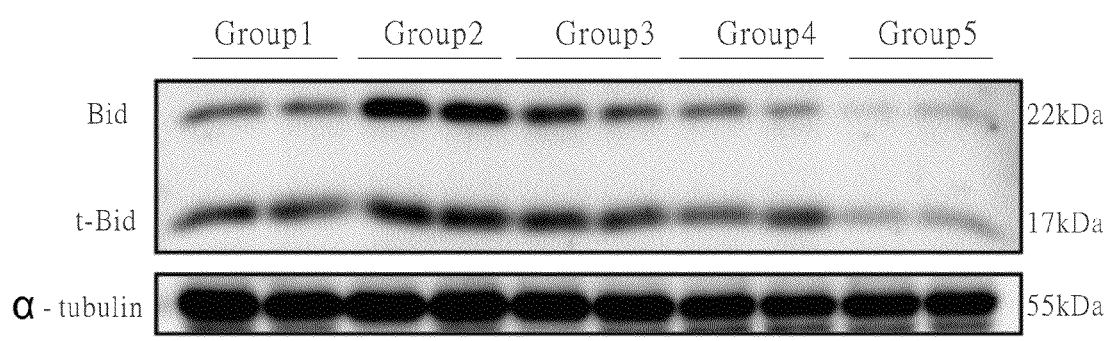
FIG. 12A is the expression of truncated BID in rat heart tissues from the groups 1 to 5.
Figure 12B:
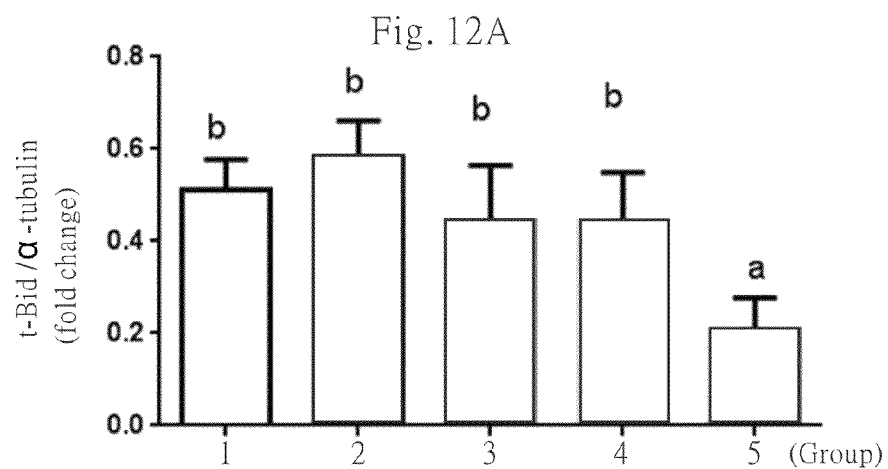
FIG. 12B is the expression level of truncated BID in rat heart tissues from the groups 1 to 5.

FIGS. 11 and 12 show that the truncated BID and activated caspase-8 largely expressed in the rat heart tissues of the group 2. The expression levels of truncated BID and activated caspase-8 of the groups 3 to 5 were all significantly lower than that of the group 2, wherein the group 5 was the lowest.

Figure 13A:
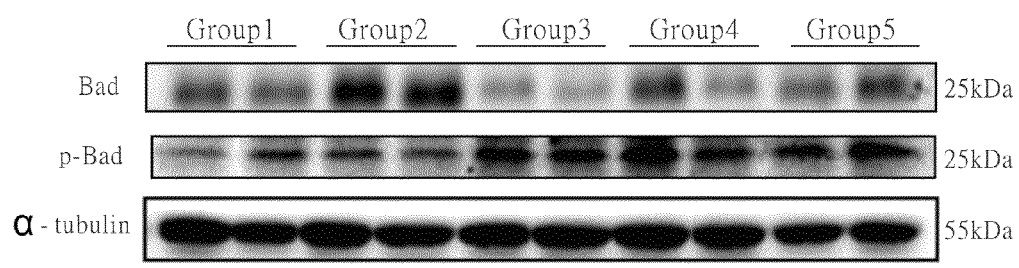
FIG. 13A is the expression of Bad in rat heart tissues from the groups 1 to 5.
Figure 13B:
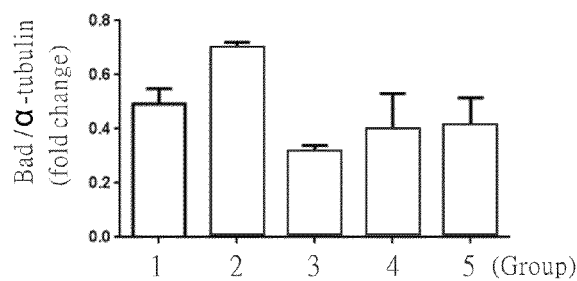
FIG. 13B is the expression level of Bad in rat heart tissues from the groups 1 to 5.
Figure 13C:
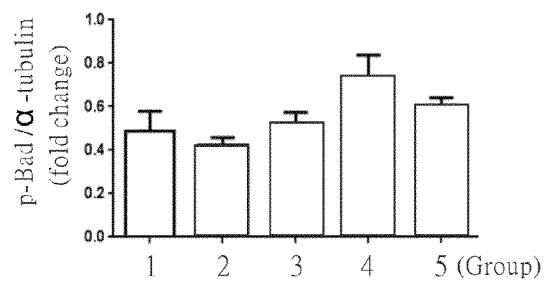
FIG. 13C is the expression level of Phospho-Bad in rat heart tissues from the groups 1 to 5.

FIG. 13 illustrates that the expression level of Bad of the group 2 was increasing in comparison with that of the group 1 and the expression level of p-Bad was decreasing in comparison with that of the group 1. In each of the groups 3 to 5, the expression level of Bad was significantly lower than the group 2 and the expression level of p-Bad was increasing in comparison with the group 2.

FIG. 14 shows that the expression levels of mitochondria related Bcl-2 and Bcl-xL of the group 2 were higher than that of the group 1. Comparing with the group 2, the expression levels of Bcl-2 or Bcl-xL of the group 3 to 5 were significantly higher, respectively.

Figure 15A:
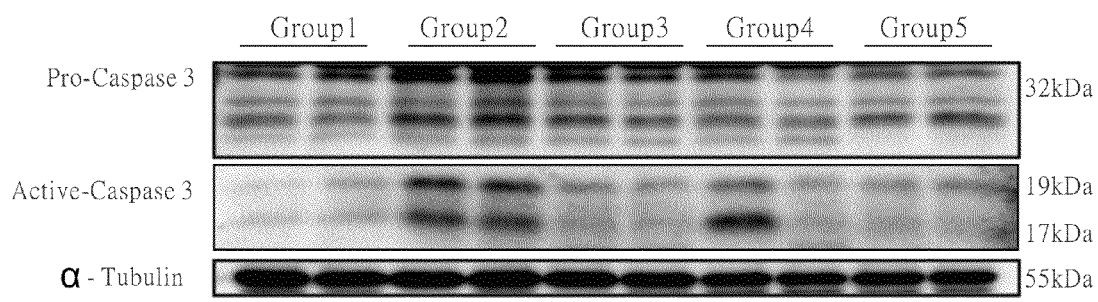
FIG. 15A is the expression of caspase 3 in rat heart tissues from the groups 1 to 5.
Figure 15B:
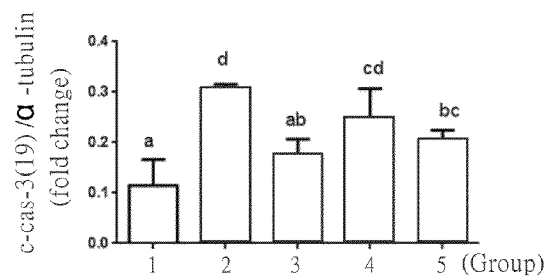
FIG. 15B is the expression level of caspase 3 in rat heart tissues from the groups 1 to 5.

FIG. 15 indicates that the expression level of activated caspase-3 of the group 2 was higher than that of the group 1 and the expression levels of activated caspase-3 of the groups 3 to 5 were significantly lower than that of the group 2, respectively.

Figure 16A:
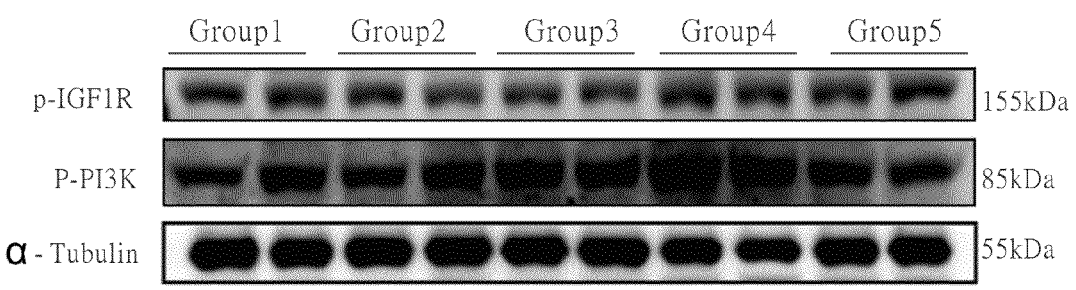
FIG. 16A is the expressions of Phospho-IGF1 receptor and Phospho-PI3K in rat heart tissues from the groups 1 to 5.
Figure 16B:
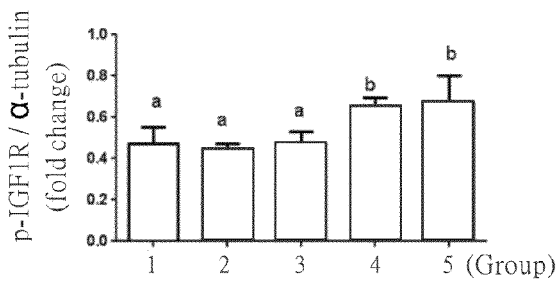
FIG. 16B is the amount of Phospho-IGF1 receptor in rat heart tissues from the groups 1 to 5.
Figure 16C:
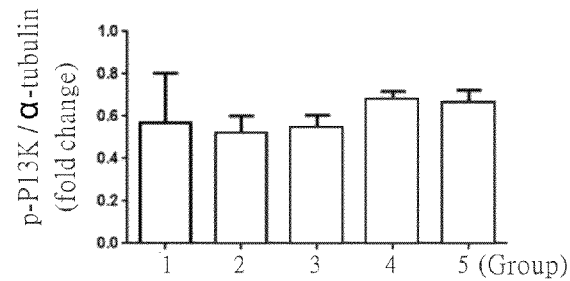
FIG. 16C is the expression levelt of Phospho-PI3K in rat heart tissues from the groups 1 to 5.
Figure 17A:
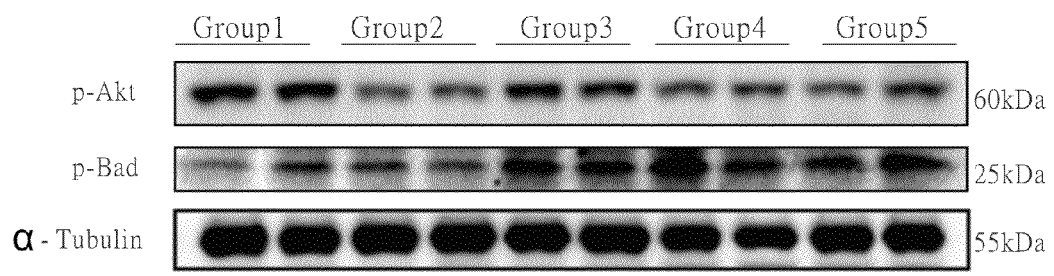
FIG. 17A is the expressions of Phospho-Bad and Phospho-Akt in rat heart tissues from the groups 1 to 5.
Figure 17B:
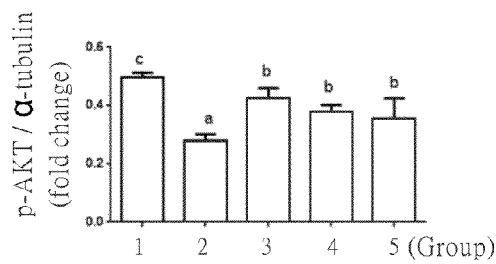
FIG. 17B is the expression level of Phospho-Akt receptor in rat heart tissues from the groups 1 to 5.
Figure 17C:
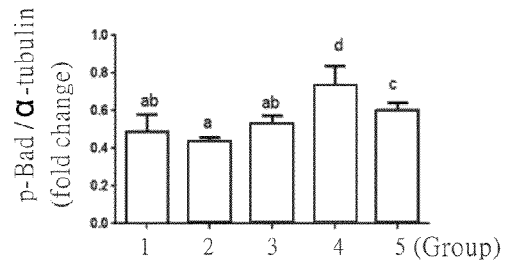
FIG. 17C is the expression level of Phospho-Bad in rat heart tissues from the groups 1 to 5.

FIGS. 16 and 17 illustrate that the expression levels of p-IGF1 receptor, p-PI3K, p-Bad or p-Akt from the myocardial cells of the group 2 were lower than that of group 1 and that of the groups 3 to 5 were respectively higher than that of the group 2.

According to the results of FIGS. 10 to 17, it shows that feeding the probiotic composition disclosed in this present invention can inhibit the expressions of proteins involved in the apoptosis pathway, like FADD, truncated BID, Bad, caspase-8, caspase-3 and increase the expressions of anti-apoptosis proteins, such as Bcl-2, Bcl-xL or p-Bad and activate and increase the amounts of PI3K or p-Akt in the pathway to survive. Therefore, the probiotic composition disclosed in this present invention can effectively reduce the myocardial apoptosis to protect myocardial cells.

From the above description, the probiotic composition of this present invention indeed has the effect to improve and protect the damages of heart tissues or myocardial apoptosis for being an effective ingredient of pharmaceutical composition to treat or prevent cardiovascular diseases or to proceed into a food for daily health care.

It should be understood that the above-mentioned detailed description and specific examples, while indicating preferred embodiments of the invention, are given by way of illustration only. Various changes and modifications within the spirit and scope of the invention will become apparent to those skilled in the art from this detailed description. All such modifications as would be obvious to one skilled in the art are intended to be included within the scope of the following claims.

What is claimed is:

1. A method for treating heart diseases, comprising administering to a subject in need thereof an effective amount of a probiotic composition to prevent damage on myocardial cells, wherein the probiotic composition comprising *Lactobacillus rhamnosus* LCR177 (BCRC910473), *Pediococcus acidilactici* PA318 (BCRC910474) and *Bifidobacterium adolescentis* (BCRC14609) in a pre-determined ratio; wherein the symptom of the heart diseases is selected from the group consisting of myocardial hypertrophy, myocardial fibrosis and myocardial apoptosis; and the ratio of *Lactobacillus rhamnosus* LCR177 (BCRC910473), *Pediococcus acidilactici* PA318 (BCRC910474) and *Bifidobacterium adolescentis* (BCRC14609) is 1:1:1.

* * * * *